United States Patent
Bonaventura et al.

(10) Patent No.: US 6,524,466 B1
(45) Date of Patent: Feb. 25, 2003

(54) METHOD AND SYSTEM OF PREVENTING FOULING AND CORROSION OF BIOMEDICAL DEVICES AND STRUCTURES

(75) Inventors: Joseph Bonaventura, Beaufort, NC (US); Louis Ignarro, Beverly Hills, CA (US); David B. Dowling, New York, NY (US); Arthur J. Spivack, Wilmington, NC (US)

(73) Assignee: Applied Semiconductor, Inc., New York, NY (US)

( * ) Notice: Subject to any disclaimer, the term of this patent is extended or adjusted under 35 U.S.C. 154(b) by 0 days.

(21) Appl. No.: 09/618,275

(22) Filed: Jul. 18, 2000

(51) Int. Cl.$^7$ ................................................. C23F 13/00
(52) U.S. Cl. ........................ 205/724; 205/725; 205/731; 205/734; 205/735; 205/740; 204/196.12; 204/196.16; 204/196.37
(58) Field of Search ................................. 205/724, 725, 205/731, 734, 735, 740; 204/196.12, 196.16, 196.37

(56) References Cited

U.S. PATENT DOCUMENTS

| | | |
|---|---|---|
| 3,562,124 A | 2/1971 | Leon et al. |
| 3,574,801 A | 4/1971 | Jauker |
| 3,620,784 A | 11/1971 | Schutt |
| 3,864,234 A | 2/1975 | Wasson |
| 4,219,358 A | 8/1980 | Hayashi et al. |
| 4,381,981 A | 5/1983 | Maes |
| 4,836,768 A | 6/1989 | Wilson et al. |
| 4,863,578 A | 9/1989 | Webster |
| 4,957,612 A | 9/1990 | Stewart et al. |
| 5,009,757 A | 4/1991 | Riffe et al. |
| 5,352,342 A | 10/1994 | Riffe |
| 5,425,867 A | 6/1995 | Dawson et al. |
| 5,496,359 A * | 3/1996 | Davidson ................ 607/115 |
| 5,500,629 A | 3/1996 | Meyer |
| 6,325,915 B1 * | 12/2001 | Dowling et al. .......... 205/724 |

OTHER PUBLICATIONS

K. Hladky, et al., "The Measurement of Localized Corrosion Using Electrochemical Noise", Corrosion and Protection Centre, UMIST, Manchester, England, pp. 1–7, www.kh-design.demon.co.uk/noise/paper1.htm, No month/year available.

"Electrochemical Noise Based Waste Tank Corrosion Monitoring", from Electrochemical Noise Based Corrosion Probe Overview, pp. 1–2, www.hanford.gov/twrs/corrosion/ec-n.htm, No month/year available.

"Electrochemical Noise Measurement System" from Non–Destructive Monitoring of Corrosion by Electrochemical Noise Measurement, 3 pp, No month/year available.

Technical Basis for Electrochemical Noise Based Corrosion Monitoring, 22 pp, No month/year available.

Chad A. Mirkin, et al., "Semiconductors meed biology", Nature, vol. 405, Jun. 2000, 4 pp.

Marc W. Mittelman, "Recovery and Characterization of Biofilm Bacteria Associated with Medical Devices", Methods in Enzymology, vol. 310, 1999, pp. 534–551, No month available.

(List continued on next page.)

*Primary Examiner*—Bruce F. Bell
(74) *Attorney, Agent, or Firm*—Oblon, Spivak, McClelland, Maier & Neustadt, P.C.

(57) ABSTRACT

A system for preventing corrosion and/or fouling of a surface of a biomedical device in contact with a corrosive environment comprising:

(a) a semiconductive coating in conductive contact with at least part of the surface; and (b) an electronic filter for filtering corrosive noise and a method of preventing corrosion and/or fouling using the system.

96 Claims, 2 Drawing Sheets

OTHER PUBLICATIONS

B.R. Mcleod, et al., "Enhanced Bacterial Biofilm control Using Electromagnetic Fields in Combination with Antibiotics", Methods in Enzymology, vol. 310, 1999, pp. 656–670, No month available.

David R. Clarke, et al., "Varistor Ceramics", J. Am. Ceram. Soc., vol. 82, No. 3, pp. 485–502, 1999, No month available.

Kirk–Othmer Encyclopedia of Chemical Technology, $4^{th}$ Ed., vol. 9, pp. 61–85 (1994), No month available.

Kirk–Othmer Encyclopedia of Chemical Technology, $4^{th}$ Ed., vol. 21, pp. 720–816 (1994), No month available.

Notification of Transmittal of International Preliminary Examination Report dated Jul. 12, 2002.

* cited by examiner

METHOD AND SYSTEM OF PREVENTING FOULING AND CORROSION OF BIOMEDICAL DEVICES AND STRUCTURES

BACKGROUND OF THE INVENTION

1. Field of the Invention

The present invention relates to a method and system for the prevention of corrosion of conductive structures using semiconductor technology, particularly where those conductive structures are part of a biomedical device in or on the body.

2. Discussion of the Background Art

A variety of methods for controlling corrosion have evolved over the past several centuries, with particular emphasis on methods to extend the life of metallic structures in corrosive environments. These methods typically include protective coatings which are used principally to upgrade the corrosion resistance of ferrous metals, such as steel, and some nonferrous metals, such as aluminum, and to avoid the necessity for using more costly alloys. Thus, they both improve performance and reduce costs. However, such protective coatings typically have several pitfalls, including poor applicability to non-metallic structures that suffer from corrosion or fouling.

Protective coatings fall into two main categories. The largest of these categories is the topical coating such as a paint, that acts as a physical barrier against the environment. The second category consists of sacrificial coatings, such as zinc or cadmium, that are designed to preferentially corrode in order to save the base metal from attack.

Cathodic protection and coatings are both engineering disciplines with a primary purpose of mitigating and preventing corrosion. Each process is different: cathodic protection prevents corrosion by introducing an electrical current from external sources to counteract the normal electrical chemical corrosion reactions whereas coatings form a barrier to prevent the flow of corrosion current or electrons between the naturally occurring anodes and cathodes or within galvanic couples. Each of these processes provided limited success. Coatings by far represent the most widespread method of general corrosion prevention (see Leon et al U.S. Pat. No. 3,562,124 and Hayashi et al U.S. Pat. No. 4,219,358). Cathodic protection, however, has been used to protect hundreds of thousands of miles of pipe and acres of steel surfaces subject to buried or immersion conditions.

The technique of cathodic protection is used to reduce the corrosion of the metal surface by providing it with enough cathodic current to make its anodic dissolution rate become negligible (for examples, see Pryor, U.S. Pat. No. 3,574,801; Wasson U.S. Pat. No. 3,864,234; Maes U.S. Pat. No. 4,381,981; Wilson et al U.S. Pat. No. 4,836,768; Webster U.S. Pat. No. 4,863,578; and Stewart et al U.S. Pat. No. 4,957,612). The cathodic protection concept operates by extinguishing the potential difference between the local anodic and cathodic surfaces through the application of sufficient current to polarize the cathodes to the potential of the anodes. In other words, the effect of applying cathodic currents is to reduce the area that continues to act as an anode, rather than reduce the rate of corrosion of such remaining anodes. Complete protection is achieved when all of the anodes have been extinguished. From an electrochemical standpoint, this indicates that sufficient electrons have been supplied to the metal to be protected, so that any tendency for the metal to ionize or go into solution has been neutralized.

Recent work in the study of corrosion has found that electrochemical corrosion processes appear to be associated with random fluctuations in the electrical properties of electrochemical systems, such as cell current and electrode potential. These random fluctuations are known in the art as "noise". Researchers have begun to apply noise analysis techniques to study the processes of corrosion in electrochemical systems.

Riffe, U.S. Pat. No. 5,352,342 and Riffe. U.S. Pat. No. 5,009,757 disclose a zinc/zinc oxide based silicate coating that is used in combination with electronics in a corrosion prevention system. The zinc/zinc oxide particles in the coating are disclosed as having semiconductor properties, primarily a p-n junction at the Zn—ZnO phase boundary. When reverse biased, this p-n junction is described as behaving as a diode and inhibiting electron transfer across the boundary. This restriction limits electron transfer from sites of Zn oxidation to the sites of oxygen reduction on the ZnO surface. Effectively, there is increased resistance between the anode and cathode of local corrosion cells and corrosion is reduced.

On average, the Zn—ZnO based junction will be reversely biased due to the potentials associated with the oxidation of Zn at the Zn surface and the reduction of $O_2$ at the ZnO surface. However, significant stochastic voltage fluctuations occur. These voltage fluctuations cause the junction to episodically become forward biased. When forward biased, electron transfer across the junction increases and there is an acceleration of the oxidation of Zn and reduction of $O_2$. Effectively, there is a short circuit between the anode and cathode of local corrosion cells and corrosion is enhanced.

The Riffe patents disclose attachment of a fixed value capacitor in the electrochemical circuit of the corrosion prevention system. However, there is no way to control the level of capacitance nor any method suggested for determining the level of capacitance needed to effectively prevent corrosion in any given structure. Hence, it is necessary to use an overcapacitance in the system to be effective.

The inside of a living organism's body is frequently thought of as reflecting the milieu of the sea, where life is thought to have arisen. As noted above, fouling and corrosion of man-made objects in the sea are subjected to a number of deleterious processes including fouling and corrosion. The fouling process is characterized by adherence and growth of both micro-and macro-organisms. Many of these same deleterious processes occur on devices that are either implanted within the bodies of humans and other living organisms or intimately associated with such devices (such as plasmapheresis systems, dialysis units and the like). The use of semiconductor materials in biological settings is only recently starting to bear useful results (see for example, Mirkin et al, *Nature*, 405, 626 (2000)). Fouling of biomedical devices and surfaces often is in the form of films of bacteria, also known as bacterial biofilms. This phenomenon has been reported by Mittelman, *Methods in Enzymology*, 310, 534–551 (1999), where the recovery and characterization of biofilm bacteria are described in connection with medical devices. One approach to treatment and control of such bacterial biofilms has been proposed by McLeod et al, *Methods in Enzymology*, 310, 656–670 (1999), by the use of a combination of electromagnetic fields with antibiotics. Unfortunately, the application of such electromagnetic fields, requiring the establishment of a current that is carefully controlled, is fine for laboratory work, but would be impractical in situ, where the real longterm effects of biofouling would be most felt.

SUMMARY OF THE INVENTION

Accordingly, one object of the present invention is to provide a semiconductive and pliable coating that provides anticorrosion and antifouling/antirejection and antibiotic properties to any conductive or nonconductive structure that is placed in the body or associated with biomedical devices.

A further object of the present invention is to provide a method for protecting conductive metallic structures from corrosion that is fine-tuned to the unique characteristics of the metallic or nonmetallic structure and its placement in the body of a living organism.

A further object of the present invention is to provide a method for preventing fouling, infection and corrosion of conductive structures by using semiconductor technology and with no external anode, no electrolyte, and no current flow.

A further object of the present invention is to provide a system for protecting conductive structures from fouling, infection and corrosion within the body, wherein the system provides long term protection with minimal system maintenance required.

These and other objects have been satisfied by the discovery of a semiconductive biologically "acceptable" coatings and associated electronic system, wherein the system can be operated by merely filtering voltage fluctuations in the conductive structure on which the semiconductive coating is placed, wherein the method for using the system comprises:

coating the conductive structure with a semiconductive coating with a fixed electronic filter connected to said coated structure, monitoring noise generated by said coating having said fixed electronic filter connected thereto, using an adjustable filter connected to said coating to determine an anti-corrosive filter response needed to minimize the noise generated by said coating; and replacing said adjustable filter with a passive or active filter having a filter response of at least said anti-corrosive filter response, wherein the conductive structure is a biomedical device attached to or implanted in a subject's body.

BRIEF DESCRIPTION OF THE FIGURES

A more complete appreciation of the invention and many of the attendant advantages thereof will be readily obtained as the same become better understood by reference to the following detailed description when considered in connection with the accompanying Figures, wherein.

DETAILED DESCRIPTION OF THE PREFERRED EMBODIMENTS

Figure 1:
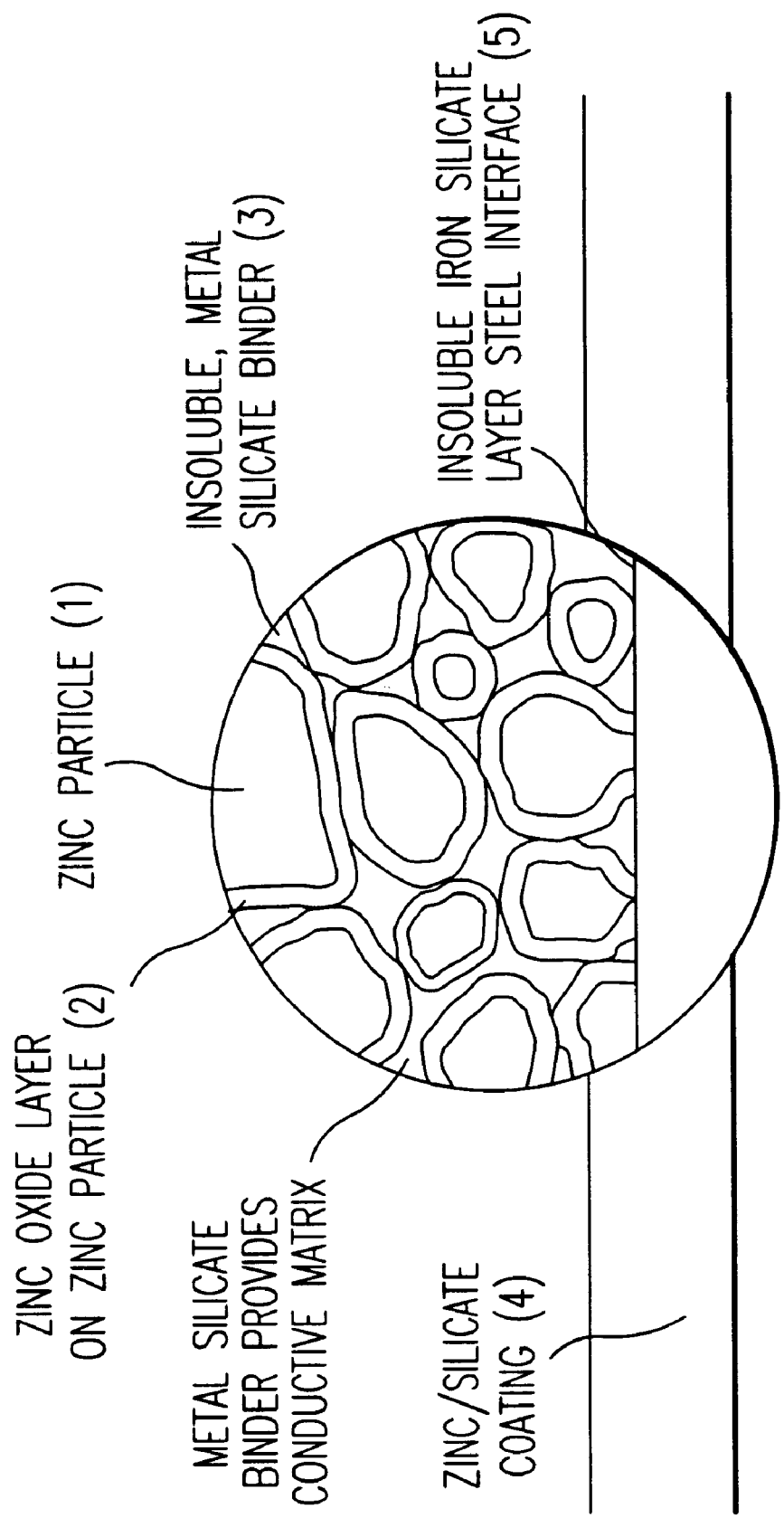
FIG. 1 is a graphical representation of the Zn/ZnO junction of a preferred embodiment of the present invention.

The present invention provides a method for the prevention of corrosion for any conductive structure susceptible to corrosion comprising coating the conductive structure with a semiconductive coating and connecting the resulting coated structure to a fixed electronic filter, monitoring the corrosive noise generated by the system, and determining the filter response needed to minimize the corrosive noise (within the context of the present invention, the term "corrosive noise" is used to describe the voltage fluctuations that occur due to the galvanic corrosion process). In one embodiment the present invention comprises adjusting the filter response using an adjustable filter to determine the filter response needed to minimize the noise generated by the coated structure, then replacing the adjustable filter with a passive electronic filter having at least the determined anticorrosive filter response. In an alternative embodiment, the invention replaces the adjustable filter with an active electronic filter and monitoring system that continuously monitors the noise and automatically adjusts the filter response to minimize the fluctuations in the system.

The present invention minimizes this corrosive noise by coupling the semiconductive coating to an electronic filter. The electronic filter has a filter response, defined within the context of the present invention as the level of reduction of noise at a given frequency. As noted above, the filter can be a passive, low-pass RC filter or an active filter. In each case, the filter minimizes the voltage fluctuations. The junctions present in the semiconductor coating then maintain a reverse bias. The time-averaged electron flow from the anodic to the cathodic domains in the semiconductive coating is then reduced and the coating is effectively passivated.

A passive, low-pass RC filter is essentially a capacitor and a resistor. In the case of the present system, the semiconductive coating acts somewhat as the resistor, with a capacitor completing the RC filter. Suitable active filters include, but are not limited to, Butterworth filters, Bessel filters, and Sallen-Key filters. These active filters are commercially available and/or can be readily prepared by those of ordinary skill in the art. These active filters are basically an op-amp circuit with capacitors. Preferably, a main component of the filters of the present invention is a capacitor, wherein the filter response is related to the capacitance needed to provide the reduction of noise at the given frequency.

The noise measurement aspects of the present invention are used to fine-tune the design of the system for specific applications. Based on the measured noise, the requisite filter properties and location of filter installation in the system can be determined and improved for consistent corrosion prevention over the entire surface of the structure, even in very large structures, such as aircraft carriers or large span bridges. In the present invention, the voltage fluctuations between the coated surface and a low-noise, high impedance reference electrode are monitored. A suitable high impedance reference electrode can be prepared from a saturated calomel electrode or a saturated sulfate electrode, for example. A commercially available high impedance reference electrode suitable for this purpose can be obtained from various catalog equipment companies, such as Beckman Instruments or Corning. The noise can be monitored using these electrodes by use of an oscilloscope to show the voltage fluctuations. Alternatively, the data obtained from the electrodes can be stored and analyzed using a PC computer with an analog-digital converter, and analyzing the resulting data using time series analysis programs, such as fast Fourier transform (FFT) analysis or a maximum entropy method (MEM method). These methods can provide both real-time and delayed results, as desired. Using such methods permits determination of the level of filter response and placement of the filters needed to generate a nearly flat line on the oscilloscope (i.e. minimize the noise). This can be done at a single location of the structure, or for finer control, at a plurality of locations around the structure surface. The electronic filter properties and filter installation locations can be adjusted to minimize the measured voltage fluctuations, thus maximizing the passivation of the coating. The ultimate result is a dramatic increase in the lifetime of the corrosion prevention system for any desired structure type. This occurs due to the reduction of the corrosive noise, thus drastically reducing the sacrificial corrosion of the semiconductive coating.

The present invention also relates to a semiconductive coating that can be used with a variety of conductive substrates to provide an array of interesting properties. The semiconductive coating of the present invention can be any semiconductive coating, including but not limited to, semiconductive coatings having (a) both n-type and p-type semiconductor domains, (b) metal-semiconductor junctions, (c) ionic conductor-semiconductor junctions, (d) metal-semiconductor-ionic conductor junctions, (e) semiconductor-insulator-semiconductor junctions, and various combinations thereof. The semiconductive coating of the present invention can be used in a variety of end uses. Chief among these end-uses is the prevention of corrosion of conductive structures. The present system for preventing corrosion of conductive substrates comprises:

(a) a semiconductor coating in conductive contact with at least part of the surface of the conductive structure; and (b) means for filtering corrosive noise, wherein the means comprise an electron sink, such as a battery or other power supply, along with a filter, such as a capacitor, connected to the coated conductive substrate and the discovery of a corrosion prevention method comprising:

1) cleaning the external surface of a conductive structure;

2) coating the external surface with the semiconductive coating of the present invention; and 3) using an electronic filter to minimize corrosive noise in the system.

The key to the method and system of the present invention is the measurement of corrosive noise generated by the entire system (including, but not limited to, the substrate, coating and filter components) and minimizing that noise by application of an electronic filter.

In the embodiment for corrosion and fouling prevention, the present system comprises two interdependent components: (1) the semiconductive coating, and (2) a means for imparting a net negative bias to the conductive structure to which the coating is applied. In general the semiconductive coating is applied to the conductive surface after it has been cleaned, preferably by grit blasting to a commercial blast finish for metal surfaces or a comparable process for non-metallic conductive structures. When a conductive surface is cleaned by grit blasting or comparable methods, the surface will have numerous grooves or indentations of from 0.1 mil up to several mil in depth. The semiconductive coating of the present invention should be applied at a depth of at least 2 mil greater than the depth of the pits formed from the cleaning process, preferably from 2 to 10 mil thickness, most preferably 7 to 9 mil thick. On smooth surfaces without significant pits, the coating can be applied at thicknesses down to about 0.5 mil without detrimentally affecting the system performance.

The structure that can be protected using the present method and system can be any conductive material susceptible to corrosion. Preferably the structure is a metallic structure of a ferrous metal or non-ferrous conductive metal. Typical metals include, but are not limited to, iron, steel, and aluminum.

The semiconductive coating of the present invention is preferably a coating of a metal or metal alloy, with or without the presence of the oxide(s) of the metal(s) present. In a most preferred embodiment, the coating is a Zn/ZnO system. The metal or metal alloy can be used on its own or combined with a suitable coating binder. Coating binders include various silicate binders, such as sodium silicate, magnesium silicate, and lithium silicate. The metal or metal alloy in the coating must have a higher oxidation potential than the conductive material to be protected. Standard electrode potentials for most metals are well known and are reproduced below for a variety of different metals.

Standard Electrode Reduction Potentials (Relative to Hydrogen Electrode)

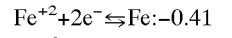
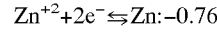
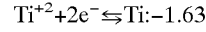
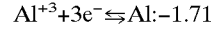
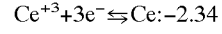
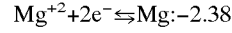
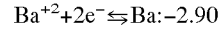
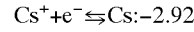

$Fe^{+2}+2e^- \rightleftharpoons Fe: -0.41$
$Zn^{+2}+2e^- \rightleftharpoons Zn: -0.76$
$Ti^{+2}+2e^- \rightleftharpoons Ti: -1.63$
$Al^{+3}+3e^- \rightleftharpoons Al: -1.71$
$Ce^{+3}+3e^- \rightleftharpoons Ce: -2.34$
$Mg^{+2}+2e^- \rightleftharpoons Mg: -2.38$
$Ba^{+2}+2e^- \rightleftharpoons Ba: -2.90$
$Cs^{+}+e^- \rightleftharpoons Cs: -2.92$ (Source: CRC Handbook of Chemistry and Physics, 60$^{th}$ ed., Ed. Robert C. Weast, CRC Press, Inc, Boca Raton, Fla., 1979)

Because the coating of the present system and method is sacrificial with respect to the conductive material being protected (although minimally sacrificial when the corrosive noise has been minimized), when determining the metal to be contained in the coating, it is important to select a metal having a standard electrode potential that is more negative than the conductive material to be protected. For example, to protect Fe (such as present in steel), the coating can use Zn, Ti or any of the other metals having a standard electrode potential more negative than −0.44. When protecting a metal having a very negative electrode potential, such as aluminum (−1.68), it is acceptable to use an alloy of a metal having a less negative electrode potential (such as Zn) combined with a metal having a more negative electrode potential (such as Mg). This alloy will provide the coating with the requisite sacrificial nature while avoiding the extreme oxidation that would occur with a coating containing only the highly negative electrode potential metal such as Mg. It is also possible to avoid a coating that is too quickly sacrificial by incorporating the highly negative electrode potential metal into one of the above noted binders. Instead of an alloy of two metals, the more negative electrode potential metal can be incorporated as the counterion of the silicate binder.

In a preferred embodiment, the semiconductive coating of the present invention can be the same coating as disclosed in Schutt, U.S. Pat. No. 3,620,784, Riffe, U.S. Pat. No. 5,352,342 or Riffe. U.S. Pat. No. 5,009,757 which are each hereby incorporated by reference. The basic building blocks of the inorganic zinc coating are silica, oxygen, and zinc. In liquid form, they are relatively small molecules of metallic silicate such as sodium silicate or organic silicate such as ethyl silicate. These essentially monomeric materials are crosslinked into a silica-oxygen-zinc structure which is the basic film former or binder for all of the inorganic zinc coatings. Suitable inorganic zinc coatings for use in the present invention are the various commercially available alkyl silicate or alkali hydrolyzed silicate types. One such commercially available coating is Carbozinc D7 WB™ manufactured by Carboline, Inc.

The coating of the present invention can also include additional n-type semiconductors incorporated into the coating, such as Sn/SnO. In addition, the coating can be doped with metals such as Al or Ga to increase the conductivity of the coating or 1–5% of Li to reduce the conductivity of the coating. The metal/metal oxide interface (Zn/ZnO) in the coating of the present invention acts as a diode in the electrochemical system. Thus, the coating contains many microdomains acting as diodes. Because of the corrosive noise generated by the coating, the diode periodically switches on and off due to fluctuations in the conductive potential of microdomains in the coating. This fluctuation of the conductive potential and switching of the diode causes the coating to corrode sacrificially. By reducing the conductivity of the coating by doping, such as with Li, it is possible to lower the switching potential of the diode to below the lowest point in the noise fluctuation curve. This will minimize the sacrificial corrosion of the coating, while still protecting the conductive material of the structure to be protected.

It may be added that by properly selecting the semiconductor coating material for a conductive surface, one can realize both the traditional passive as well as the novel active barriers.

In a preferred embodiment, the zinc dust of the coating of the present invention forms a metal-semiconductor junction where the zinc metal and zinc oxide interface, with the zinc oxide being an n-type semiconductor.

A preferred embodiment of the completed coating is schematically shown in FIG. 1. FIG. 1 shows the porous nature of the preferred zinc/zinc oxide/silicate coating (4) of the present invention. The zinc particles (1) are covered by a zinc oxide layer (2) with the various oxide coated particles surrounded by an insoluble metal silicate binder (3). At the interface (5) between the coating and the structure metal, is an insoluble metal silicate layer, which in the case of a steel structure would be an insoluble iron silicate layer.

The conductive structure of the present invention can be any conductive structure in need of protection from corrosion, including both metal structures and non-metal structures. Examples of such metal structures include metal vehicles, such as ships, planes, automobiles, military tanks or transports, metal vehicle parts, bridges, railroad coupling mechanisms, containers, pipes and metal towers, as well as smaller structures such as biomedical devices. Examples of metal vehicle parts include metal parts of vehicles such as automobiles, airplanes, trains, military land vehicles such as tanks, and ships and other marine vehicles. Examples of containers are refinery containers, storage silos and storage bins. Examples of non-metal conductive structures include conductive concrete and conductive polymeric structures. Corrosive processes also affect these non-metal conductive structures and can also be minimized by the present invention. Conductive concrete has been proposed as a possible material for preparation of floating airport runways. The system of the present invention would help prevent corrosion of the concrete, thus extending the life and structural integrity of the concrete structures.

In addition, the present system permits prevention of corrosion of biomedical devices within the body of a living organism, preferably the human body. One difficulty that is encountered in the implantation of metal or non-metal based conductive biomedical devices is corrosion of the devices under the conditions found in the human body. Within the context of the present invention, the term "biomedical devices" includes both devices that are implanted into the body as well as any device external to the body and subjected to bodily fluids causing potential surface corrosion of the device. Suitable examples include artificial joints, artificial organs and any other devices used to treat a subject in sub-optimal health.

By coating the surface of the device with the semiconductive coating of the present invention and connecting the requisite fixed electronic filter, the device can be fine-tuned in vivo using the adjustable filter and noise measurement of the present invention. For example, upon implantation and connection of the fixed electronic filter to the biomedical device, the noise can be measured and minimized using the adjustable filter. At that point, prior to completion of the implantation procedure, the noise measuring means and adjustable filter can be removed and a fixed passive or active filter having the requisite filter response attached. The filter can be housed externally, or even internally if desired, much as is done with pacemakers. Further the power supply for the electronic system could be as simple as a pacemaker battery pack, a single AAA battery, or even a microbattery such as the thin-film battery described in Bates et al, U.S. Pat. No. 5,338,625, hereby incorporated by reference, which would have sufficient power to operate the system for several years. Any type of battery could be used, including alkaline, NiCd, and other rechargeable batteries. Use of thin-film batteries such as those of Bates et al would allow application of the battery directly onto the surface of the semiconductor coating, allowing for the most compact complete package.

In the biomedical embodiments, the semiconductive coating would be applied to the surface of the device, whether it is made of metal, such as titanium or the stainless steels frequently used in biomedical devices, or made of a non-metal conductive material, such as a polymer composite material having conductive properties. Such polymer composite materials would include polymeric devices containing conductive carbon fiber in the polymer, carbon fiber-epoxy composites, carbon nanotube-epoxy composites, and other polymeric materials having conductive carbon embedded therein. Other suitable polymeric materials would include any polymeric material that is physiologically acceptable, including, but not limited to, silicones, Teflon, Kel-F and other highly fluorinated polymers. Highly flexible polymers could also be used, since the semiconductive coatings have a significant degree of flexibility when coated on a surface. Coating of the semiconductor coating onto the polymeric materials could be performed using conventional methods.

One significant advantage obtained in the present invention is that by minimizing the sacrificial corrosion of the semiconductive coating, the life of the coating will be extended to be many times longer than that of conventional coating protection systems. While this would be possible to achieve under water through the application of cathodic current, it would require substantial current and would be very difficult to control. Further, the cathodic current model would not be practical for biomedical embodiments, due to the difficulties associated with maintaining such a current in the body. The method of the present invention functions internally to the coating and thus prevents atmospheric corrosion where the corroding medium is nothing more than moisture condensed from the air. This becomes extremely important in protecting such surfaces as the internal surfaces of modern ships, where designs to provide increased strengths have concomitantly increased corrosion prone areas, and in protecting automobile parts, bridges, airplanes, and trains. This would also provide significant impact in the anti-fouling properties of the coating, since by fine-tuning the duty cycle of the electronic system and minimizing the sacrificial corrosion, the level of metal ions released from the surface (i.e. providing a locally toxic environment to fouling organisms), is minimized and can even be stopped on a macro scale, even though the metal ions may be released and readhered by the electronic cycling on a micro scale. Other metals that are significantly more toxic than the more preferred zinc coating, such as Hg/HgO, Cd/CdO and the like, could then be used for the anti-fouling benefits in the body, while avoiding the toxic effects on the body as a whole. Combinations of these metals could likewise be used to provide optimum antifouling and anticorrosion benefits.

Another preferred embodiment is the use of the present method and system on the internal surfaces of modern ships where the condensation is most corrosive due to its high saline content and where, at the same time, there is insufficient moisture for cathodic protection systems to function. Without the noise filter of the present invention, the zinc in the coating would quickly leach out and be eroded away by the flow of condensate to the bilges. However, upon the application of a noise filter in accordance with the present invention to the metallic substrate, this leaching is effectively halted.

Additionally, the use of a noise filter on the substrate steel of the ship provides no greater interference to shipboard electronics than turning on a light bulb within the ship, nor would it yield a detectable signal to hostile detection devices, since the noise filter, even those that use a battery or other source of electrons, does not produce a field that would radiate perceptibly beyond the coating. The absorbance characteristics of zinc are well known and are often used for EM shielding and electronics enclosures. Thus, there would also be no measurable EM radiation from shore-based structures to which the present system is applied.

The fixed electronic filter of the present invention acts as a capacitor having an electron sink attached thereto to keep the capacitor reverse biased. The fixed electronic filter is preferably a combination of a conventional power supply, for example a direct current (DC) power supply means such as a battery, preferably a 12 Volt battery, and solar cells and alternating current (AC) power supply means. It is to be noted that although this component is termed a "power supply" in the present description, there is no current and no voltage in the present system. Accordingly, the power supply nomenclature is merely for convenience and is not intended to imply electron flow. The power supply means used preferably would be sufficient to deliver a voltage of from 0.5 to 30 V, most preferably 10 to 20 V, if a completed circuit were available. The fixed electronic filter (i.e., power supply and capacitor) can be connected to the coated conductive substrate, either directly to the substrate or to the coating. In a preferred embodiment, the power supply means of the present invention has a negative terminal directly coupled to the conductive structure to be protected. The positive terminal of the power supply means is coupled to the conductive structure by way of the filter/capacitor, to a portion of the structure remote from the negative terminal connection. Since the present invention does not rely on creation of current flow, which drops off as the distance between terminals increases, the distance between the terminals is not critical, so long as the positive and negative terminals do not touch one another. The positive terminal connection is preferably made to a location on the structure from 0.01 meter to 30 meters from the location of the negative terminal connection, most preferably from 5 to 10 meters from the location of the negative terminal connection.

The method of the present invention is self-tending for the life of the system. There are no currents or potentials to monitor and control periodically as there would be in a conventional cathodic protection system. Further, there is no possibility that the present system can go out of control and severely damage the supporting structures as can occur in an impressed cathodic protection system. The only effective reduction in the life of the coating would therefore come from wind and water-borne abrasion. Since the abrasion resistance of the coating is somewhat better than that of galvanize, the life expectancy of the coating can be extended to the range of several decades.

Additionally, with the use of an active filter and monitoring system that continually monitors noise fluctuations and adjusts the filter properties, such as filter response and cutoff frequency, the coating lifetime can be extended by preventing increases in the rate of sacrificial loss due to increases in corrosion over time.

Figure 2:
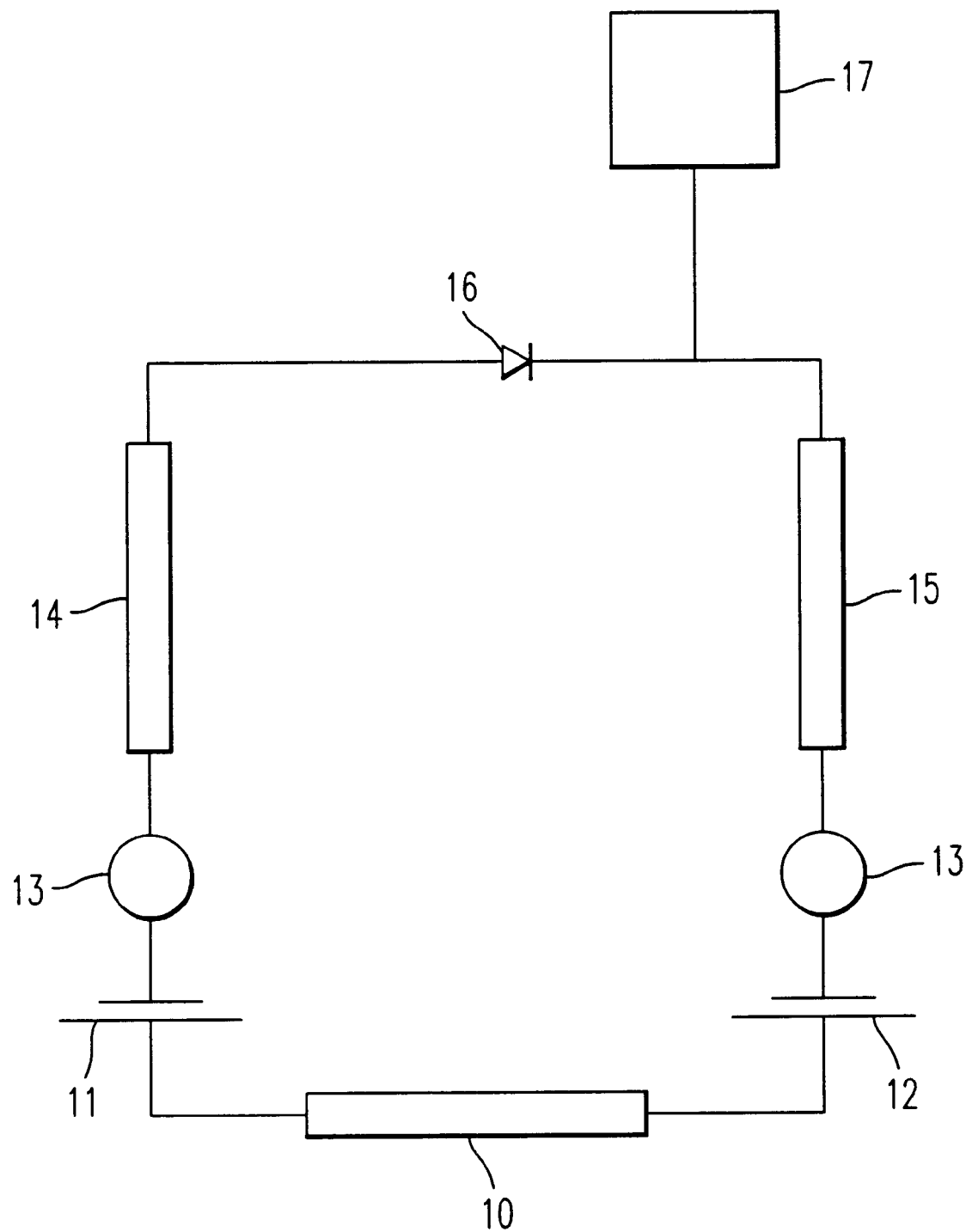
FIG. 2 shows an equivalent circuit diagram depicting the system of the present invention.

FIG. 2 shows an equivalent circuit diagram depicting the system of the present invention. In the circuit, 10 is the Solution resistance (Rs), with 11 and 12 being the galvanic electrode potential at the anode (Ea) and cathode (Ec), respectively. The noise source (En) in the circuit is represented by 13. The faradaic impedance of the anode (Ra) and cathode (Rc) are shown in 14 and 15, respectively. The metal-semiconductor junction at the Zn/ZnO boundary is shown as diode (D) 16. The noise filter (F), whether active or passive filter, is represented by 17.

Obviously, numerous modifications and variations of the present invention are possible in light of the above teachings. It is therefore to be understood that within the scope of the appended claims, the invention may be practiced otherwise than as specifically described herein.

What is claimed is:

1. A method for preventing corrosion of a conductive surface of a biomedical device in contact with a corrosive environment, said method comprising:
    (a) coating the conductive surface with a semiconductive coating and providing an electronic filter connected to the coated conductive structure;
    (b) monitoring corrosive noise generated by the coated conductive structure and adjusting filter properties of said electronic filter to minimize the corrosive noise, wherein said conductive surface is a surface of a biomedical device selected from the group consisting of artificial joints, and organs.

2. The method of claim 1, wherein said electronic filter comprises a power source and a capacitor.

3. The method of claim 1, wherein said monitoring and adjusting step (b) is performed continually using an active filter and monitoring means.

4. The method of claim 1, wherein said electronic filter comprises a plurality of capacitors and said step (b) further comprises determining a placement of each of said plurality of capacitors on said conductive surface.

5. The method of claim 1, wherein said conductive surface is a metal conductive surface.

6. The method of claim 5, wherein said metal conductive surface comprises a metal selected from the group consisting of ferrous metals and conductive non-ferrous metals.

7. The method of claim 6, wherein said metal is steel.

8. The method of claim 6, wherein said metal is aluminum.

9. The method of claim 6, wherein said metal is stainless steel.

10. The method of claim 6, wherein said metal is titanium.

11. The method of claim 1, wherein said conductive surface is a non-metallic conductive material.

12. The method of claim 11, wherein said non-metallic conductive material is a carbon fiber-epoxy composite.

13. The method of claim 11, wherein said non-metallic conductive material is a carbon nanotube-epoxy composite.

14. The method of claim 11, wherein said non-metallic conductive material is conductive carbon embedded in a physiologically acceptable polymer.

15. The method of claim 1, wherein said semiconductive coating contains both p-type and n-type semiconductor domains.

16. The method of claim 1, wherein said semiconductive coating contains a metal-semiconductor junction.

17. The method of claim 1, wherein said semiconductive coating contains an ionic conductor-semiconductor junction.

18. The method of claim 1, wherein said semiconductive coating contains a metal-semiconductor-ionic conductor junction.

19. The method of claim 1, wherein said semiconductive coating contains a semiconductor-insulator-semiconductor junction.

20. The method of claim 1, wherein said semiconductive coating is a metal/metal oxide/silicate coating.

21. The method of claim 20, wherein said metal/metal oxide/silicate coating is a zinc/zinc oxide/silicate coating.

22. The method of claim 20, wherein said zinc/zinc oxide/silicate coating comprises zinc in an amount of from 80–92% by weight based on dry coating.

23. The method of claim 22, wherein said zinc/zinc oxide/silicate coating comprises zinc in an amount of from 85–89% by weight based on dry coating.

24. The method of claim 20, wherein said metal/metal oxide/silicate coating comprises a metal selected from the group consisting of Zn, Ti, Al, Ga, Ce, Mg, Ba and Cs, and the corresponding metal oxide.

25. The method of claim 24, wherein said metal/metal oxide/silicate coating comprises a mixture of one or more metals selected from the group consisting of Zn, Ti, Al, Ga, Ce, Mg, Ba and Cs and one or more metal oxides obtained therefrom.

26. The method of claim 24, wherein said semiconductive coating further comprises one or more dopants.

27. A system for preventing corrosion or fouling or both of a biomedical device, comprising:
(a) a biomedical device having thereon a semiconductive coating, wherein said biomedical device is a member selected from the group consisting of artificial joints, and organs;
(b) a fixed electronic filter;
(c) a corrosive noise monitoring system; and
(d) an adjustable filter.

28. The system of claim 27, wherein said corrosive noise monitoring system further comprises a high impedance reference electrode and an oscilloscope.

29. The system of claim 27, wherein said adjustable filter is selected from the group consisting of manually adjustable filters and active filters.

30. The system of claim 27, wherein said semiconductive coating contains both p-type and n-type semiconductor domains.

31. The system of claim 27, wherein said semiconductive coating contains a metal-semiconductor junction.

32. The system of claim 27, wherein said semiconductive coating contains an ionic conductor-semiconductor junction.

33. The system of claim 27, wherein said semiconductive coating contains a metal-semiconductor-ionic conductor junction.

34. The system of claim 27, wherein said semiconductive coating contains a semiconductor-insulator-semiconductor junction.

35. The system of claim 27, wherein said semiconductive coating is a metal/metal oxide/silicate coating.

36. The system of claim 35, wherein said metal/metal oxide/silicate coating is a zinc/zinc oxide/silicate coating.

37. The system of claim 36, wherein said zinc/zinc oxide/silicate coating comprises zinc in an amount of from 80–92% by weight based on dry coating.

38. The system of claim 37, wherein said zinc/zinc oxide/silicate coating comprises zinc in an amount of from 85–89% by weight based on dry coating.

39. The system of claim 35, wherein said metal/metal oxide/silicate coating comprises a metal selected from the group consisting of Zn, Ti, Al, Ga, Ce, Mg, Ba and Cs and the corresponding metal oxide.

40. The system of claim 39, wherein said metal/metal oxide/silicate coating comprises a mixture of one or more metals selected from the group consisting of Zn, Ti, Al, Ga, Ce, Mg, Ba and Cs and one or more metal oxides obtained therefrom.

41. The system of claim 39, wherein said semiconductive coating further comprises one or more dopants.

42. The system of claim 27, wherein said conductive surface is a metal conductive surface.

43. The system of claim 42, wherein said metal conductive surface comprises a metal selected from the group consisting of ferrous metals and conductive non-ferrous metals.

44. The system of claim 43, wherein said metal is steel.

45. The system of claim 43, wherein said metal is aluminum.

46. The system of claim 43, wherein said metal is stainless steel.

47. The system of claim 43, wherein said metal is titanium.

48. The system of claim 27, wherein said conductive surface is a non-metallic conductive material.

49. The system of claim 48, wherein said non-metallic conductive material is a carbon fiber-epoxy composite.

50. The system of claim 48, wherein said non-metallic conductive material is a carbon nanotube-epoxy composite.

51. The system of claim 48, wherein said non-metallic conductive material is conductive carbon embedded in a physiologically acceptable polymer.

52. A method for preventing corrosion of a conductive surface of a biomedical device in contact with a corrosive environment, said method comprising:
(a) coating the conductive surface with a semiconductive coating and providing an electronic filter connected to the coated conductive structure;
(b) monitoring corrosive noise generated by the coated conductive structure and adjusting filter properties of said electronic filter to minimize the corrosive noise
wherein the conductive surface is a surface made of a material selected from the group consisting of stainless steel, titanium and non-metallic conductive materials.

53. The method of claim 52, wherein said electronic filter comprises a power source and a capacitor.

54. The method of claim 52, wherein said monitoring and adjusting step (b) is performed continually using an active filter and monitoring means.

55. The method of claim 52, wherein said electronic filter comprises a plurality of capacitors and said step (b) further comprises determining a placement of each of said plurality of capacitors on said conductive surface.

56. The method of claim 52, wherein said conductive surface is stainless steel.

57. The method of claim 52, wherein said conductive surface is titanium.

58. The method of claim 52, wherein said conductive surface is a non-metallic conductive material.

59. The method of claim 58, wherein said non-metallic conductive material is a carbon fiber-epoxy composite.

60. The method of claim 58, wherein said non-metallic conductive material is a carbon nanotube-epoxy composite.

61. The method of claim 58, wherein said non-metallic conductive material is conductive carbon embedded in a physiologically acceptable polymer.

62. The method of claim 52, wherein said conductive surface is a surface of a biomedical device selected from the group consisting of artificial joints, and organs.

63. The method of claim 52, wherein said semiconductive coating contains both p-type and n-type semiconductor domains.

64. The method of claim 52, wherein said semiconductive coating contains a metal-semiconductor junction.

65. The method of claim 52, wherein said semiconductive coating contains an ionic conductor-semiconductor junction.

66. The method of claim 52, wherein said semiconductive coating contains a metal-semiconductor-ionic conductor junction.

67. The method of claim 52, wherein said semiconductive coating contains a semiconductor-insulator-semiconductor junction.

68. The method of claim 52, wherein said semiconductive coating is a metal/metal oxide/silicate coating.

69. The method of claim 68, wherein said metal/metal oxide/silicate coating is a zinc/zinc oxide/silicate coating.

70. The method of claim 68, wherein said zinc/zinc oxide/silicate coating comprises zinc in an amount of from 80–92% by weight based on dry coating.

71. The method of claim 70, wherein said zinc/zinc oxide/silicate coating comprises zinc in an amount of from 85–89% by weight based on dry coating.

72. The method of claim 68, wherein said metal/metal oxide/silicate coating comprises a metal selected from the group consisting of Zn, Ti, Al, Ga, Ce, Mg, Ba and Cs, and the corresponding metal oxide.

73. The method of claim 72, wherein said metal/metal oxide/silicate coating comprises a mixture of one or more metals selected from the group consisting of Zn, Ti, Al, Ga, Ce, Mg, Ba and Cs and one or more metal oxides obtained therefrom.

74. The method of claim 73, wherein said semiconductive coating further comprises one or more dopants.

75. A system for preventing corrosion or fouling or both of a biomedical device, comprising:
   (a) a biomedical device having, on a conductive surface thereof, a semiconductive coating, wherein said conductive surface is a material selected from the group consisting of stainless steel, titanium and non-metallic conductive materials;
   (b) a fixed electronic filter;
   (c) a corrosive noise monitoring system; and
   (d) an adjustable filter.

76. The system of claim 75, wherein said corrosive noise monitoring system further comprises a high impedance reference electrode and an oscilloscope.

77. The system of claim 75, wherein said adjustable filter is selected from the group consisting of manually adjustable filters and active filters.

78. The system of claim 75, wherein said semiconductive coating contains both p-type and n-type semiconductor domains.

79. The system of claim 75, wherein said semiconductive coating contains a metal-semiconductor junction.

80. The system of claim 75, wherein said semiconductive coating contains an ionic conductor-semiconductor junction.

81. The system of claim 75, wherein said semiconductive coating contains a metal-semiconductor-ionic conductor junction.

82. The system of claim 75, wherein said semiconductive coating contains a semiconductor-insulator-semiconductor junction.

83. The system of claim 75, wherein said semiconductive coating is a metal/metal oxide/silicate coating.

84. The system of claim 83, wherein said metal/metal oxide/silicate coating is a zinc/zinc oxide/silicate coating.

85. The system of claim 84, wherein said zinc/zinc oxide/silicate coating comprises zinc in an amount of from 80–92% by weight based on dry coating.

86. The system of claim 85, wherein said zinc/zinc oxide/silicate coating comprises zinc in an amount of from 85–89% by weight based on dry coating.

87. The system of claim 83, wherein said metal/metal oxide/silicate coating comprises a metal selected from the group consisting of Zn, Ti, Al, Ga, Ce, Mg, Ba and Cs and the corresponding metal oxide.

88. The system of claim 87, wherein said metal/metal oxide/silicate coating comprises a mixture of one or more metals selected from the group consisting of Zn, Ti, Al, Ga, Ce, Mg, Ba and Cs and one or more metal oxides obtained therefrom.

89. The system of claim 87, wherein said semiconductive coating further comprises one or more dopants.

90. The system of claim 75, wherein said conductive surface is stainless steel.

91. The system of claim 75, wherein said conductive surface is titanium.

92. The system of claim 75, wherein said conductive surface is a non-metallic conductive material.

93. The system of claim 92, wherein said non-metallic conductive material is a carbon fiber-epoxy composite.

94. The system of claim 92, wherein said non-metallic conductive material is a carbon nanotube-epoxy composite.

95. The system of claim 92, wherein said non-metallic conductive material is conductive carbon embedded in a physiologically acceptable polymer.

96. The system of claim 75, wherein said conductive surface is a surface of a biomedical device selected from the group consisting of artificial joints, and organs.

* * * * *